United States Patent
Uchikubo

(10) Patent No.: US 6,950,691 B2
(45) Date of Patent: Sep. 27, 2005

(54) SURGERY SUPPORT SYSTEM AND SURGERY SUPPORT METHOD

(75) Inventor: Akinobu Uchikubo, Iruma (JP)

(73) Assignee: Olympus Corporation, Tokyo (JP)

( * ) Notice: Subject to any disclaimer, the term of this patent is extended or adjusted under 35 U.S.C. 154(b) by 516 days.

(21) Appl. No.: 10/120,269

(22) Filed: Apr. 10, 2002

(65) Prior Publication Data

US 2002/0147384 A1 Oct. 10, 2002

(30) Foreign Application Priority Data

Apr. 10, 2001 (JP) ........................................ 2001-111749

(51) Int. Cl.[7] ................................................. A61B 5/05
(52) U.S. Cl. ..................................... 600/427; 600/424
(58) Field of Search ............................... 600/427, 424, 600/425, 407, 410, 411, 414, 426

(56) References Cited

U.S. PATENT DOCUMENTS

| | | | | |
|---|---|---|---|---|
| 6,014,580 A | * | 1/2000 | Blume et al. | 600/424 |
| 6,298,262 B1 | * | 10/2001 | Franck et al. | 600/426 |
| 6,490,467 B1 | * | 12/2002 | Bucholz et al. | 600/407 |
| 6,529,765 B1 | * | 3/2003 | Franck et al. | 600/427 |
| 6,546,277 B1 | * | 4/2003 | Franck et al. | 600/426 |
| 6,580,938 B1 | * | 6/2003 | Acker | 600/424 |
| 6,614,453 B1 | * | 9/2003 | Suri et al. | 715/764 |
| 6,687,531 B1 | * | 2/2004 | Ferre et al. | 600/424 |
| 6,694,167 B1 | * | 2/2004 | Ferre et al. | 600/424 |

FOREIGN PATENT DOCUMENTS

JP 2000-245738 9/2000

* cited by examiner

*Primary Examiner*—Daniel Robinson
(74) *Attorney, Agent, or Firm*—Scully, Scott, Murphy & Presser

(57) ABSTRACT

A first controller synthesizes image output of a CCU and a cursor created based on trigger information from a second controller, following location information. The synthesized image is displayed on a first monitor, so an endoscope image and a cursor image which moves synchronously with the cursor image on a display device can be simultaneously viewed at the surgery room side on a single monitor, and accordingly, the problem of the working space inside the surgery room becoming crowded due to providing multiple observation monitors in the surgery room does not occur.

14 Claims, 12 Drawing Sheets

SURGERY SUPPORT SYSTEM AND SURGERY SUPPORT METHOD

This application claims benefit of Japanese Application No. 2001-111749 filed on Apr. 10, 2001, the contents of which are incorporated by this reference.

BACKGROUND OF THE INVENTION

1. Field of the Invention

The present invention relates to a surgery support system and surgery support method, and particularly relates to a surgery support system and surgery support method for supporting surgery.

2. Description of the Related Art

Normally, surgery is performed on a patient by a surgeon in a surgery room. However, a system is being conceived for cases such as, for example, a surgeon in the surgery room needing to perform surgery regarding which he/she has little experience, wherein the surgeon is connected by a communication line with a surgeon skilled in the particular surgery at a remote location,(hereafter referred to as "remote support surgeon"), so that the surgeon in the surgery room can perform the surgery under the remote support of the remote support surgeon such as instructions on parts to be removed, so appropriate surgery can be performed on the patient in the surgery room.

An example of a remote surgery support system for supporting surgery in such a remote matter is disclosed in Japanese Unexamined Patent Application Publication No. 2000-245738.

The art disclosed therein requires that a first monitor means for displaying output images of an endoscope camera, and the second monitor means for displaying images transferred from the remote location, be installed in the surgery room.

Now, when endoscopic surgery is being performed, the surgery room is filled with much equipment. Accordingly, newly installing such equipment in the surgery room could worsen the surgery environment. On the other hand, there has been need for the surgeon to observe the endoscope images and images from the remote location on separate monitors. With endoscopic surgery, the direction of the hands of the surgeon and the location where the observation monitor is installed may not be in the same direction, which is not a suitable arrangement for surgery. Moreover, with remote surgery support, a further monitor is installed next to the main observation monitor, so the surgeon has been forced to observe monitors in an even more unnatural manner.

The present invention has been made in light of the above, and accordingly, it is an object thereof to provide a surgery support system and surgery support method wherein endoscope observation images and instruction information from a remote location can be integrated displayed on a single monitor without inviting deterioration in the working environment of the surgery room when performing remote surgery support to instruct surgery from a remote location side via a communication line.

SUMMARY OF THE INVENTION

To this end, the surgery support system according to the present invention for performing communication of information regarding surgery and supporting surgery, comprises: an imaging device for taking images of a, treatment region of a patient, and outputting picture signals; a first, display device for displaying images of the treatment region, based on picture signals output from the imaging device; a first transmitting circuit for transmitting picture signals output from the imaging device to a communication line; a first receiving circuit for receiving the picture signals from the first transmitting circuit via the communication line; a second display device for displaying images of the treatment region, based on picture signals received with the first receiving circuit; a first pointer superimposing circuit for superimposing a first pointer for instructing location on the second display device display the treatment region; an operating unit for moving the first pointer displayed on the second display device by the first pointer superimposing circuit; a second transmitting circuit for transmitting location information of the first pointer to the communication line; a second receiving circuit for receiving location information of the first pointer from the second transmitting circuit via the communication line; and a second pointer superimposing circuit for superimposing a second pointer on the first display device, based on location information received with the second receiving circuit.

The above and other objects, features and advantages of the invention will become more clearly understood from the following description referring to the accompanying drawings.

DESCRIPTION OF THE PREFERRED EMBODIMENTS

The following is a description of embodiments of the present invention, with reference to the drawings.

Figure 1:
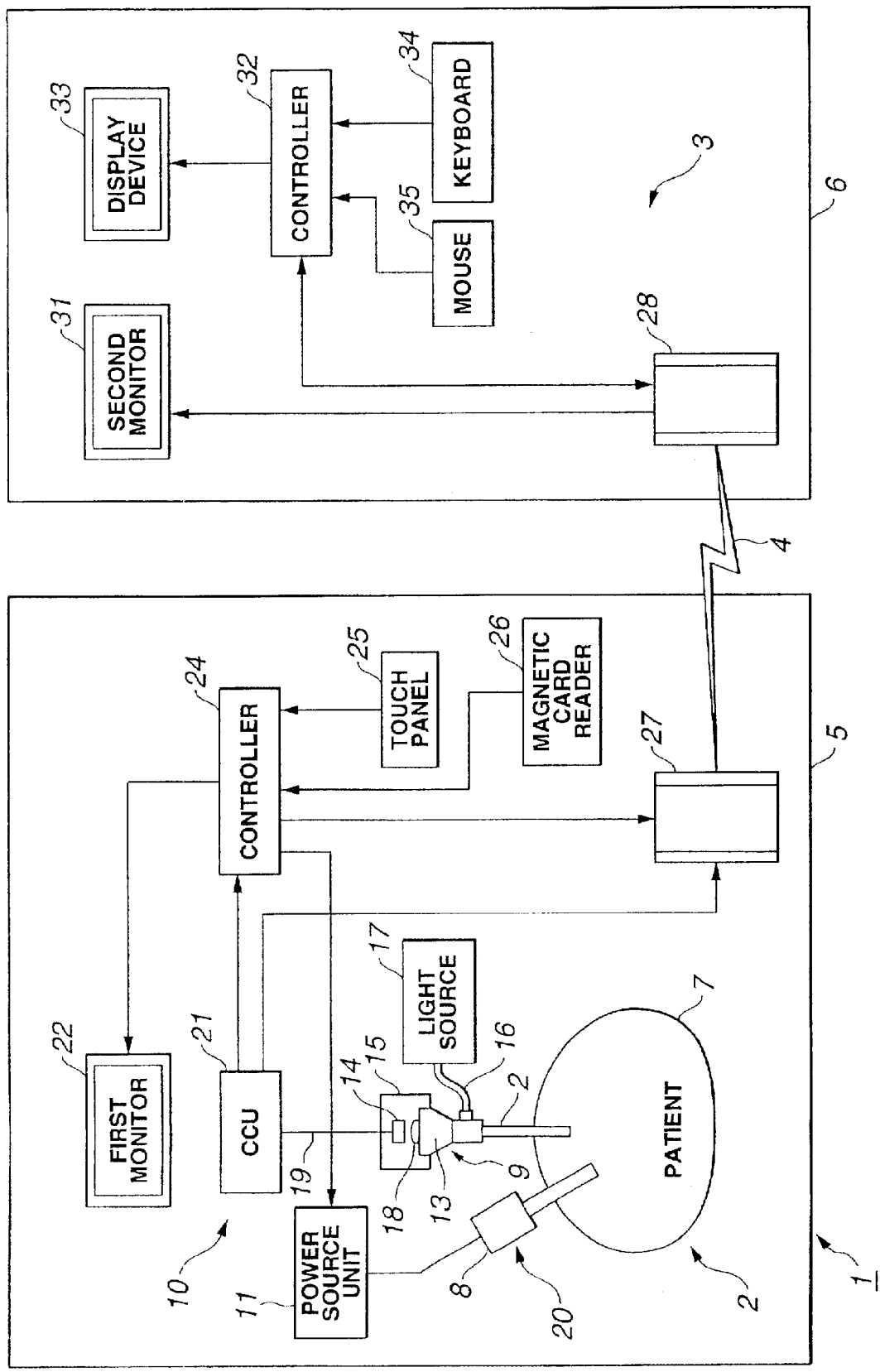
FIG. 1 is a configuration diagram illustrating the configuration of the remote surgery support system according to a first embodiment of the present invention.
Figure 2:
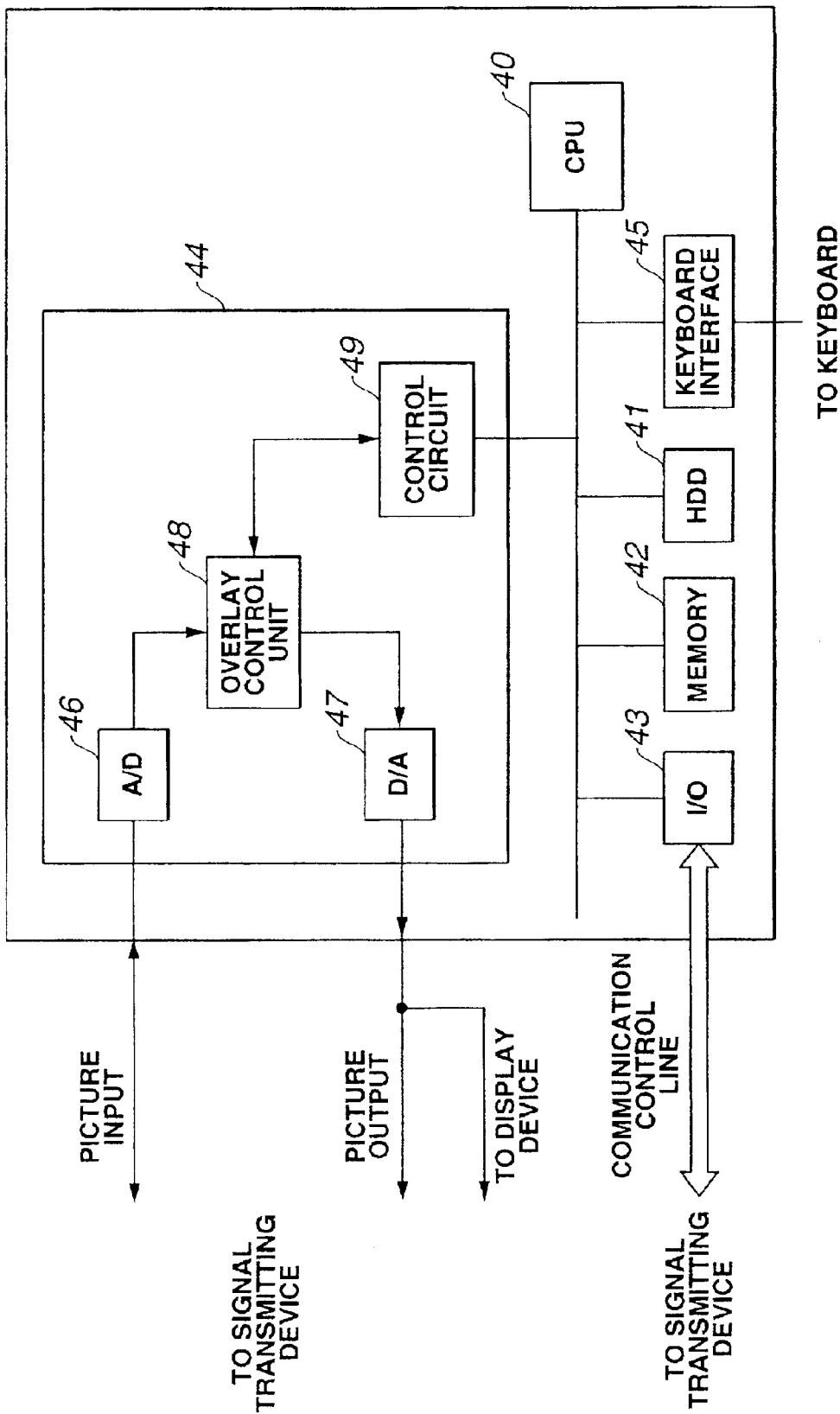
FIG. 2 is a configuration diagram illustrating the configuration of a second controller at a remote support device side show in FIG. 1.
Figure 3:
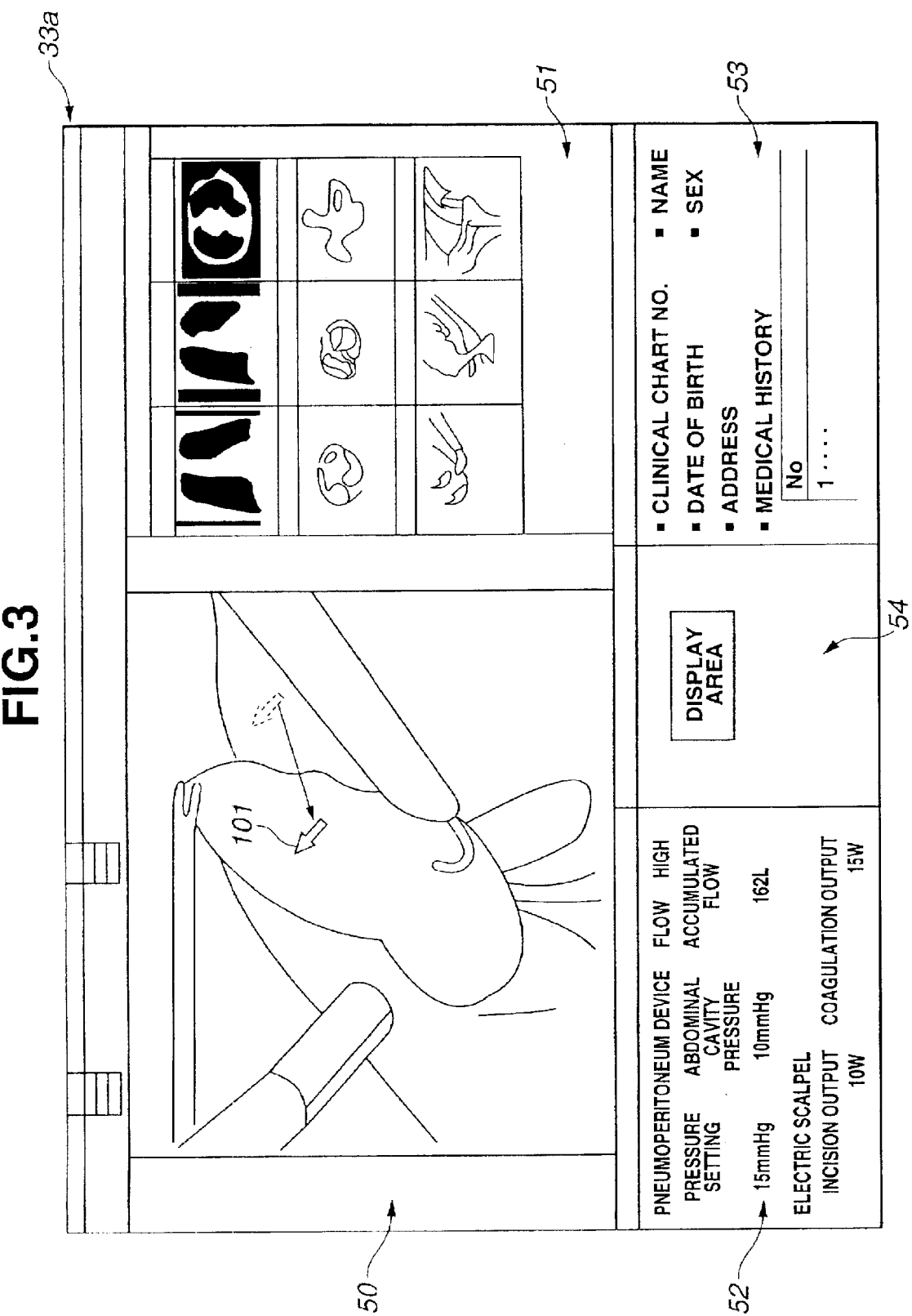
FIG. 3 is a diagram illustrating a first screen display example for describing a cursor displayed on the display screen of the display device shown in FIG. 1.
Figure 4:
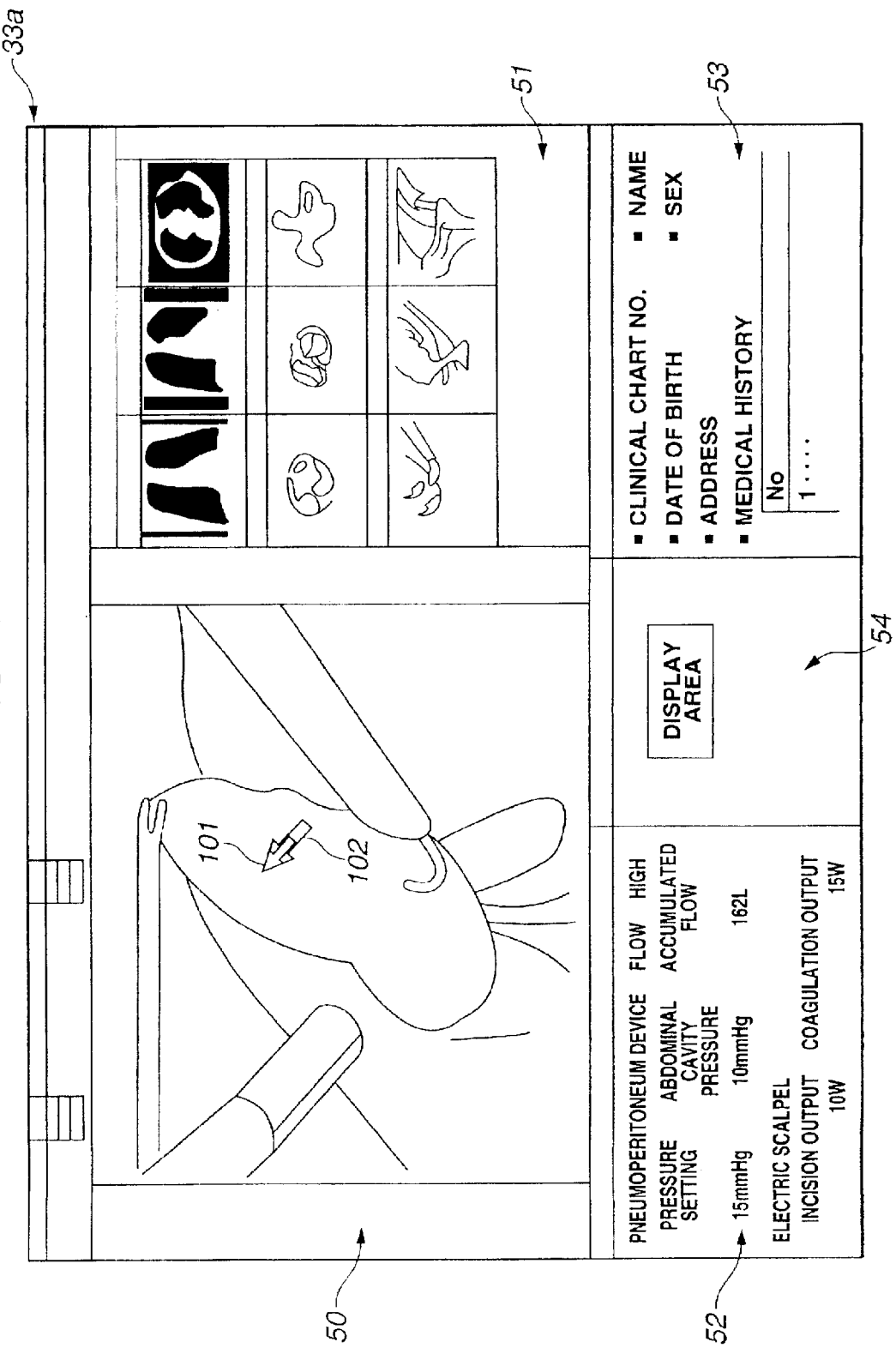
FIG. 4 is a diagram illustrating a second screen display example for describing a cursor displayed on the display screen of the display device shown in FIG. 1.
Figure 5:
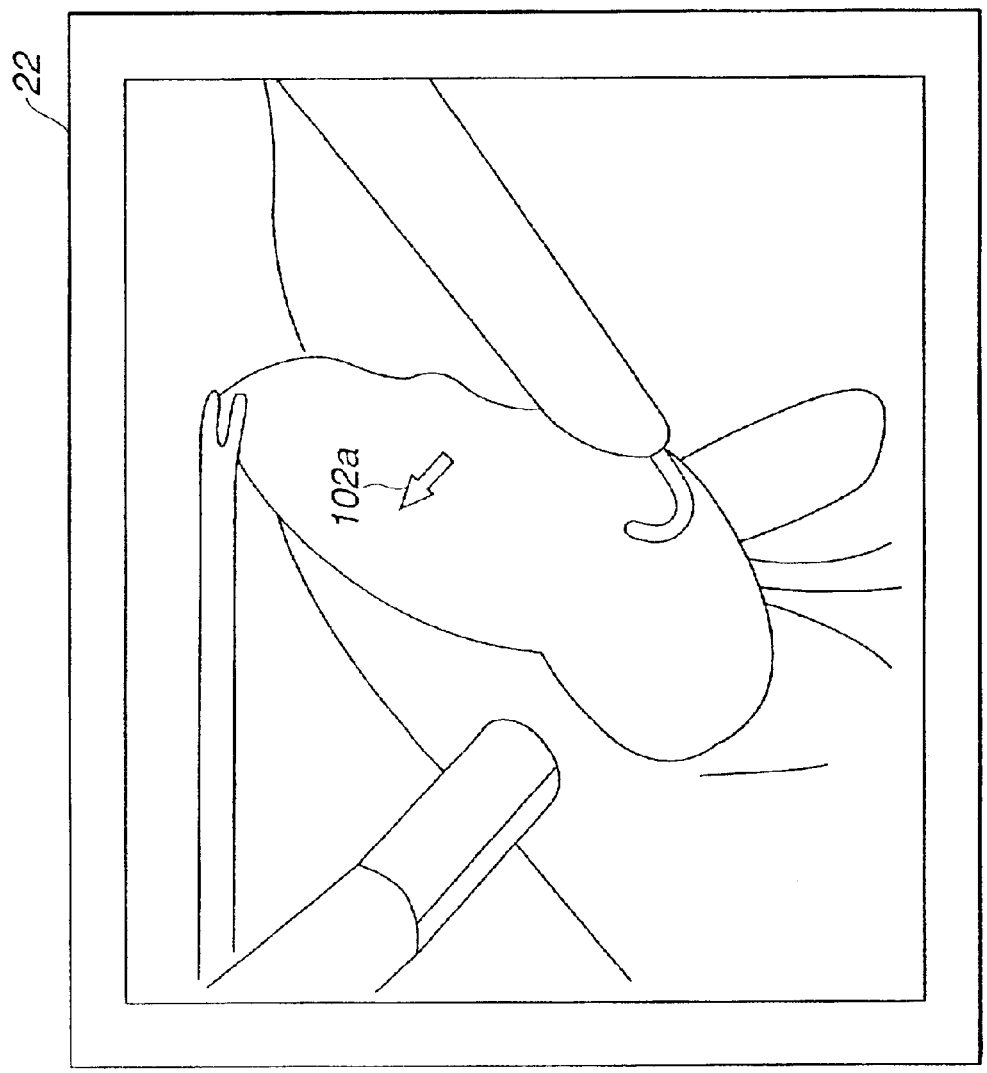
FIG. 5 is a diagram illustrating a first screen display example for describing a cursor displayed on the first monitor shown in FIG. 1.
Figure 6:
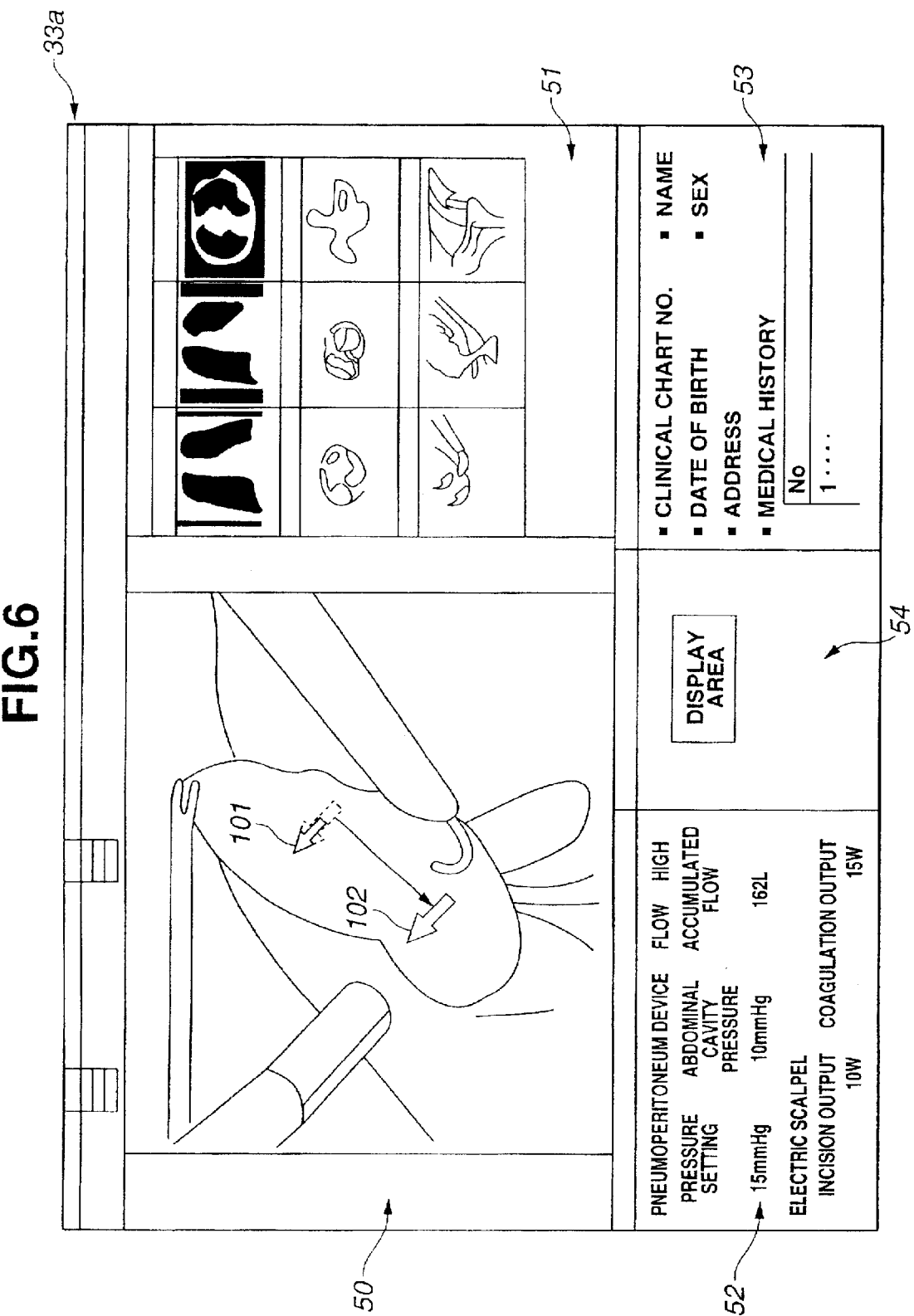
FIG. 6 is a diagram illustrating a third screen display example for describing a cursor displayed on the display screen of the display device shown in FIG. 1.
Figure 7:
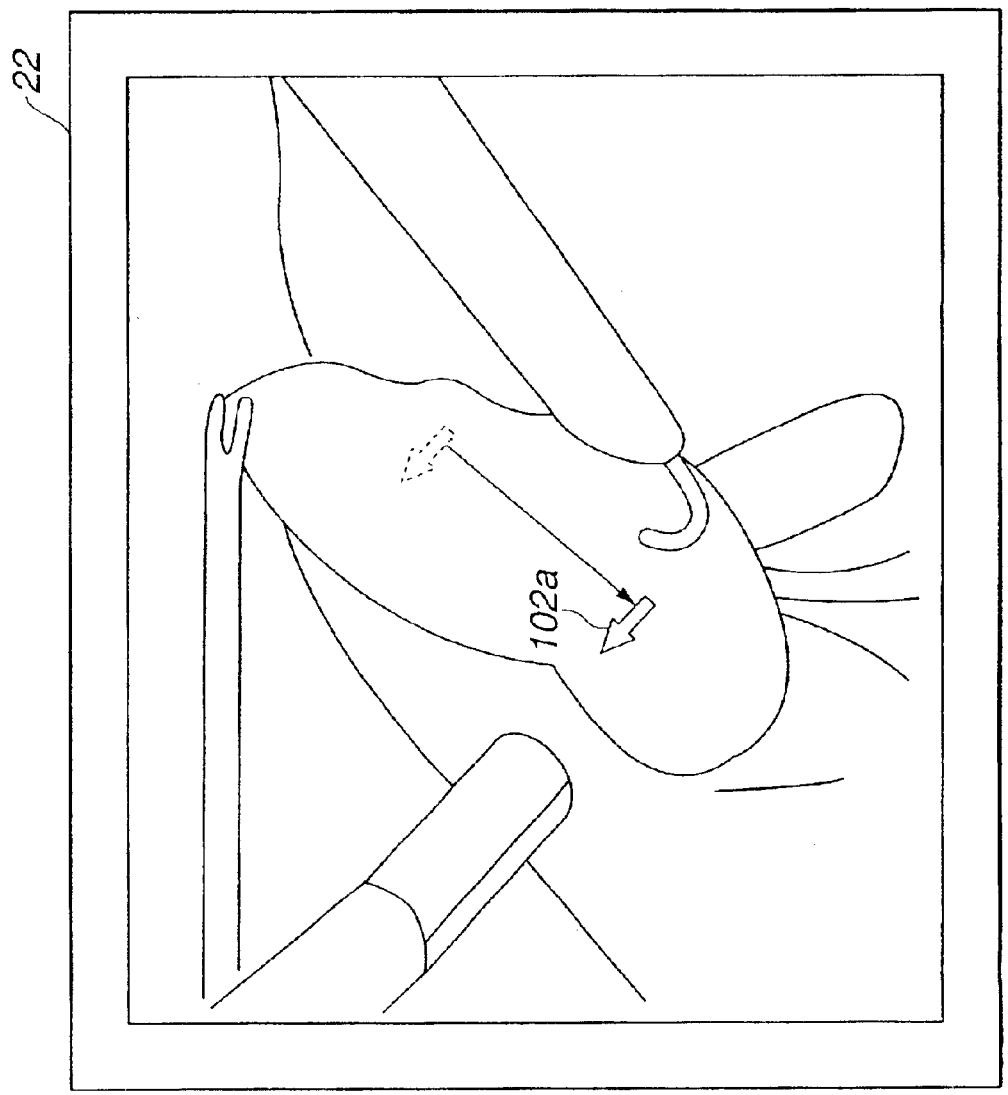
FIG. 7 is a diagram illustrating a second screen display example for describing a cursor displayed on the first monitor shown in FIG. 1.
Figure 8:
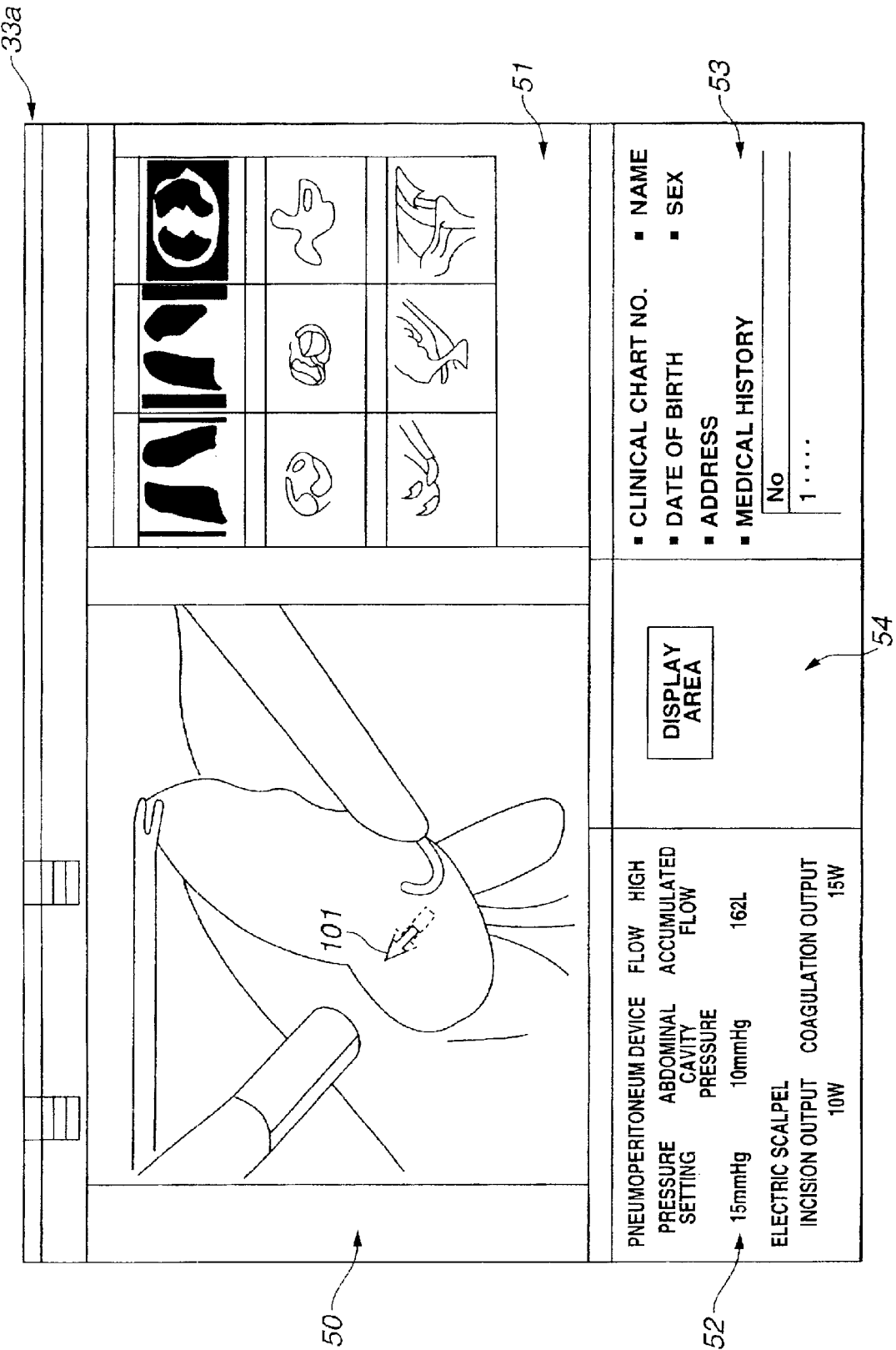
FIG. 8 is a diagram illustrating a fourth screen display example for describing a cursor displayed on the display screen of the display device shown in FIG. 1.

FIGS. 1 through 8 relate to a first embodiment of the present invention, wherein FIG. 1 is a configuration diagram illustrating the configuration of the remote surgery support system according to a first embodiment of the present invention, FIG. 2 is a configuration diagram illustrating the configuration of a second controller at a remote support device side shown in FIG. 1, FIG. 3 is a diagram illustrating a first screen display example for describing a cursor displayed on the display screen of the display device shown in FIG. 1, FIG. 4 is a diagram illustrating a second screen display example for describing a cursor displayed on the display screen of the display device shown in FIG. 1, FIG. 5 is a diagram illustrating a first screen display example for describing a cursor displayed on the first monitor shown in FIG. 1, FIG. 6 is a diagram illustrating a third screen display example for describing a cursor displayed on the display screen of the display device shown in FIG. 1, FIG. 7 is a diagram illustrating a second screen display example for describing a cursor displayed on the first monitor shown in FIG. 1, and FIG. 8 is a diagram illustrating a fourth screen display example for describing a cursor displayed on the display screen of the display device shown in FIG. 1.

The present embodiment is a remote surgery support system wherein the surgery room and the remote control room at a remote location are connected via a communication line, with a surgeon in the surgery room receiving support information from the remote control room side to perform surgery.

As shown in FIG. 1, the remote surgery support system 1 according to the first embodiment of the present invention is configured of a surgery device unit 2, and a remote support device unit 3 which is in the remote location from this surgery device unit 2, connected with a network line 4. The surgery device unit 2 and the remote support device unit 3 are disposed in the surgery room 5 and remote control room (remote support device room) 6, respectively.

The surgery device unit 2 installed in the surgery room 5 comprises an endoscope imaging device 10 for observing within the body cavities of a patient, and surgery device (surgical equipment) 20 for performing a surgery for treating the patient, under observation of the endoscope image device 10.

More specifically, a surgical equipment main unit 8 for performing treatment surgery, and an optical endoscope 9 for observing the state of the surgery and so forth with this surgical equipment main unit 8, are inserted into the abdomen, for example, of the patient 7. The surgical equipment main unit 8 is a device such as an electric scalpel or the like for performing incisions or coagulation or like operations, the surgical equipment main unit 8 being connected with an electric power source unit 11 for supplying driving electric power source to the surgical equipment main unit 8 and having functions wherein output setting values are variable according to the incisions or coagulation modes, via a cord or the like, the surgical equipment main unit 8 and the electric power source unit (control unit, depending on the treatment equipment) 11 making up the surgical equipment 20.

Also, the endoscope 9 is a rigid endoscope having a hard insertion portion 12, for example, with a television camera 15 with a built-in charge-coupled device (hereafter referred to as a "CCD") 14, for example, mounted as an imaging device at an eyepiece 13 provided at the rear end side of the insertion portion 12, thereby forming means for taking endoscope images.

A light guide cable 16 Of the endoscope 9 is connected to a light source device 17, transferring illumination light of an unshown lamp within the light source device 17 to a light guide within the light guide cable 16 and a light guide within the endoscope 9, so as to cast the illumination light that has been transferred from a light guide tip window fixed at an illumination window at the tip side of the insertion portion 12, thereby illuminating the subject side, which is the internal organs in the body cavity, or the like.

An unshown object lens is attached to the observation window adjacent to the illumination window, for image-formation of an optical image. This optical image is transferred backwards by a relay lens system, for example, serving as an optical image transferring means disposed within the insertion portion 12, and can be enlarged and observed via an unshown ocular lens at the eyepiece 13.

The transferred optical image is subjected to image formation at the CCD 14, via an image-forming lens 18 of a television camera 15 which is detachably mounted to the eyepiece 13. This CCD 14 is connected with a camera control unit (hereafter referred to as "CCU") 21 via a signal cable 19, and the signals subjected to photo-electric conversion at the CCD 14 are then subjected to signal processing, thereby making up an endoscope image-taking device 20 which generates standard picture signals (video signals).

The picture signals from the CCU 14 are output to a first controller 24, and an endoscope image, which is the internal organs in the body cavity forming the treatment portion of the patient, and the tip side of the surgical equipment main unit 8 for operating on the internal organs in the body cavity, taken with the CCD 14, are displayed on a first monitor 22 via the first controller 24.

Also, the CCU 21 and electric power source unit 11 are also connected to the first controller 24 which performs control and the like thereof. This controller 24 is also connected with a touch panel 25 for example for performing instruction input of control, and the magnetic card reader 26 for example for performing input and the like of patient data.

For example, the surgeon can perform control such as changing the tone by the CCU 21 of the control 24 by operating the touch panel 25, and can also perform output control and the like for the surgical equipment main unit 8. In the event that the surgical equipment main unit 8 is an elector scalpel, for example, the surgeon can perform setting control of that output level thereof so as to perform incisions, coagulation, etc., with the electric scalpel. Also, in the event that the treatment equipment 20 is a pneumoperitoneum device, the surgeon can perform control for changing and setting the pressure values and so forth.

Also, patient data recorded in a magnetic card can be read by the magnetic card reader 26, the patient data input to the controller 24, with the controller 24 superimposing the patient data on the endoscope image from the CCU 21.

Also this CCU 21 and the controller 24 provided in the surgery room 5 are connected with the first signal transmitting device 27. Endoscope images output from the CCU 21 are displayed on the first monitor 22 via the controller 24. This arrangement also allows picture signals of the endoscope images to be converted into signals transmittable by a broadband network line 4, such as an ATM (Asynchronous Transfer Mode) line by a signal transmitting device 27, and transmitted to a second signal transmitting device 28 at the remote control room 6 side via the network line 4.

Also, the signals transmitted from the signal transmitting device 28 at the remote control room 6 side to the signal transmitting device 27 via the network line 4 are converted into picture signals, output to the first monitor 22 connected via the controller 24 connected to the signal transmitting device 27, and can display the image information and the like from the signal transmitting device 28 side on the first monitor 22 in a superimposed manner.

Also, the control signals or patient data or the like from the controller 24 are converted into signals transmittable over the network line 4 by the signal transmitting device 27, and can be transmitted to the signal transmitting device 28 at the remote control room 6 side via the network line 4.

Also, an unshown keyboard, mouse, etc., are also connected to the controller 24, so that cursor location information and the like can be transmitted from the mouse to the remote surgeon side at the signal transmitting device 28 side via the controller 24.

On the other hand, a second monitor 31 is connected to the signal transmitting device 28 at the remote support device 3 within the remote control room 6, and endoscope images sent from the CCU 21, for example, at the surgery room 5 side, are displayed on the second monitor 31.

Also, this signal transmitting device 28 is connected with a second controller 32, and a display device 33 serving as a third monitor is connected to the controller 32. Also, input means such as a touch panel, or keyboard 34, and the like, for example, are connected to this controller 32. Further connected is a pointing device, such as a mouse 35.

The controller 32 captures still images of the endoscope images being sent from the CCU 21 at the surgery room 5 side via the signal transmitting devices 27 and 28, and also receives input of patient information and the like transmitted from the first controller 24 via the signal transmitting devices 27 and 28. The controller 32 displays the still images and the patient information or the like on the display unit 33 by superimposing or the like, and also makes display input with the input means such as the keyboard 34 or mouse 35 or the like for providing support information such as instruction information or the like at the time of the surgery, for the surgeon at the surgery room 5 side, for example. For example, display input is made by marking locations for excision, the location of arteries to watch out for at the time of the excision, and so forth. The controller 32 makes an overly display of a cursor image at a position based on this display input on the display device 33, i.e. superimposes the cursor image on the endoscope image.

Also, information relating to the marked image displayed in an overlaid manner on the display device 33, information such as the location of the cursor, the orientation of the cursor, the size of the cursor, the color of the cursor, etc., is transmitted to the first controller 24 within the surgery room 5 via the signal transmitting devices 28 and 27. The first controller 24 superimposes the cursor image at the desired location on the image output of the CCU 21, according to the information relating to the marked image, and displays this on the first monitor 22.

Thus, the surgeon in the surgery room 5 can carry out appropriate surgery by performing the surgery while observing the endoscope image upon which the support information from the remote support surgeon has been superimposed, on the first monitor 22.

FIG. 2 is a configuration diagram illustrating the configuration of the controller 32. This controller 32 is made up of the a Central Processing Unit (hereafter referred to as "CPU") 40 for performing controlling operations, a hard disk drive (hereafter referred to as "HDD") 41 for storing operation programs for the CPU 40, images, etc., memory 42 used for temporary storage of images, work area, etc., an input/output interface (hereafter referred to as "I/O") 43 for performing input and output via the signal transmitting device 28 video capture control unit 44 for performing capturing operations and superimposed display operations of picture signals, and a keyboard interface (hereafter referred to as keyboard I/F) 45 connected with a keyboard 34, for example, and these components are mutually connected via a bus.

Communication of control signals or the like from the second signal transmitting device 28 is performed via the I/O 43. Operating programs for the controller 32 are stored in the HDD 41. In the event of making settings for controlling the operations of the surgical equipment 20 from the touch panel 25 or the like at the surgery room 5 side, for example, via the first controller 24, the control contents thereof are stored in memory 42 or the like from the I/O 43 within the controller 32 via the signal transmitting devices 27 and 28. Also, patient information is also stored in memory 42 or the like from the I/O 43 within the controller 32 in the same way.

Also, the video capture control unit 44 is connected with a signal transmitting device 28 and has an A/D converter 46 for performing A/D conversion of input video signals, and a D/A converter 47 for performing D/A conversion of video signals and outputting.

The A/D converter 46 and a D/A converter 47 are connected with an overlay control unit 48 for performing overlay control, and this overly control unit 48 has video memory therein and is connected to a control circuit 49 for performing control of the overlay display and exchange and the like of data. Also, this control circuit 49 is connected to the bus.

With the present embodiment, image communication by the signal transmitting device 28 is performed via the A/D converter 46 and D/A converter 47 making up the video capture control unit 44. Picture signals input from the A/D converter 46 are subjected to image conversion following control of the control circuit 49 at the overlay control unit 48.

The output of the overlay control unit 48 is transmitted to the signal transmitting device 28 via the D/A converter 47. Communication between this signal transmitting device 28 and the controller 32 is controlled by the CPU 40, following programs stored in the HDD 41.

Also, images captured via the video capture control unit 44 can be stored in a HDD 41. Also, reduced images of images stored in the HDD 41, such as thumbnail images for example, selected from the keyboard 34, may be output to the video capture control unit 44 side and superimposed on picture signals transmitted from the first signal transmitting device 27 side by the CPU 40, via the overlay control unit 48.

Also, picture signals from the D/A converter 47 are output to the display device 33 as well, and a display such as shown in FIG. 3 for example may be made to on this display device 33.

A display area 33a of the display device 33 is made up of an image display area 50, thumbnail display area 51, surgical equipment state display area 52, patient information display area 53, and comment display area 54.

The thumbnail display area 51 is an area for displaying multiple images relating to items selected by a operating an image selection button (not shown) displayed in a tool bar in the display area 33a, displaying an image window, and selecting the desired item (patient named, name of technique, etc.).

Picture signals from the CCU 21 making up the endoscope imaging means and images selected from the thumbnail display area 51 are displayed in the image display area 50.

Displayed in the thumbnail display area 51 are reduced screens and moving images of image data stored in the second controller 32, and picture images corresponding to the endoscope image from the CCU 21 in reduced still images (thumbnail images).

The surgical equipment state display area 52 displays the state of the surgical equipment main unit 8 transmitted from the first controller 24, the CCU 21, and so forth.

Patient information from the first controller 24 is displayed in the patient information display area 53.

Note that ATM (Asynchronous Transfer Mode) or TCP/IP can be conceived as a means for transmitting the images, audio, and signals over the network line 4.

The operation of the present embodiment having such a configuration will be described. As shown in FIG. 1, the surgery device unit 2 and the remote support device unit 3 are connected by a network line 4 such as an ATM, and the power sources are turned on. Also, patient information such as the name of the patient 7 is input to the first controller 24 from the magnetic card reader 26.

The endoscope 9 is connected to the light source device 17 via the light guide cable 16 so as to supply the illumination light, the television camera 15 is mounted to the eyepiece 13 of the endoscope 9 and the signal cable 19 of the television camera 15 is connected to the CCU 21, so that endoscope images taken by the CCD 14 via the first controller 24 are displayed on the first monitor 22.

First, the pneumoperitoneum device is inserted into the abdomen of the patient 7 via an unshown trocar, and pneumoperitoneum is performed in the abdomen. Then, the insertion portion 12 of the endoscope 9 is inserted via the trocar, so that the part to be treated within the abdomen is displayed on the first monitor 22.

Also, the surgical equipment main unit 8 such as the electorate scalpel or the like with which that abdomen of the patient 7 is to be operated on is inserted via the trocar.

In the event of changing the tone of the endoscope image displayed on the first monitor 22, the surgeon can operate the touch panel 25 to send control signals from the first controller 24 to the CCU 21, thereby changing the tone.

The picture signals of the endoscope image output from the CCU 21 to the first monitor 22 are transmitted from the first signal transmitting device 27 to the second signal transmitting device 28 side via the line 4, and displayed on the second monitor 31.

The connections are arranged so that the picture signals can be input to the second controller 32. In the event that the endoscope image displayed on the second monitor 31 is a suitable image displaying the part for excision in the surgery for example, the remote support surgeon makes capture instructions from the keyboard 34 to capture the endoscope image (still image) via the video capture control unit 44 of the controller 32. The captured endoscope image is displayed on the image display area 50 of the display device 33 connected to this controller 32, as shown in FIG. 3.

Also, patient information from the magnetic card reader 26 is input to the controller 32 from the first controller 24 via the signal transmitting devices 27 and 28, from the I/O 43 thereof, and stored in memory 42 or the like, for example, within this controller 32. The patient information is always displayed in a patient information display area 53 on the display device 33, as shown in FIG. 3.

Also, the remote support surgeon makes an overlay. display of the endoscope images and patient information and the like sent from the surgery room 5 side on the display device 33, sets the location for excision in the event that treatment area is to be removed with the surgical equipment main unit 8 in a still image state, and marks on the still image by making input from the mouse 35 or keyboard 34 or the like, or marks arteries regarding which care should be taken near the part to be excised with a different color from the part to be excised, and so forth, thereby displaying support information.

Also, the output values set for excision using an electric scalpel for example, and the output values set for coagulation thereof, are set by the surgeon in the surgery room 5 from the touch panel 25. This causes the control contents including that output settings for the surgery equipment 20 to be transmitted from the first controller 24 to the I/O 43 of the second controller 32, and stored in memory 42 or the like, for example, and control information which is setting information for the surgery equipment 20 is displayed in the surgery equipment state display area 52, as shown in FIG. 3.

Also, in FIG. 3, setting information for the pneumoperitoneum device is also displayed in the surgery equipment state display area 52. That is to say, control information for multiple pieces of surgical equipment can be displayed.

Also, upon the surgeon in the surgery room 5 making settings for changing or the like of the output values of the electric scalpel from the touch panel 25, the changed contents are sent to the I/O 43 of the second controller 32, and updated contents are displayed in the surgery equipment state display area 52. That is, the control contents of the surgical equipment 20, i.e., the settings contents are displayed on the display device 33 in an almost real-time manner, so the state of the surgical equipment 20 can be confirmed by the remote support surgeon in an almost real-time manner.

Also, in the event that the surgeon in the surgery room 5 inputs comments or the like from the keyboard or the like, the comments are displayed on the comment display area 54 as shown in FIG. 3.

In the event that a reply from the remote support, surgeon is desired for this comment, the remote support surgeon attaches a reply and transmits this to the surgery room 5 side, so the surgeon in the surgery room 5 can confirm this by making reference or the like to the first monitor 22.

Also, the remote support surgeon can record endoscope images captured by the video capture control unit 44, and the still images thereof are recorded on the HDD 41 upon making input of instructions for recording from the keyboard 34, for example.

Also, the endoscope images stored in the HDD 41 can be reduced and reduced images selected for display may be displayed in the thumbnail display area 51 shown in FIG. 3.

Also, besides endoscope images, X-ray images or the like of the patient 7 may be transmitted to the second controller 32 in the remote control room 6 from the first controller 24, so as to make display of reduced images of the images stored in the HDD 41.

The remote support surgeon can make accurate diagnosis for surgery on the patient 7 by making reference to these images and the like on the display device 33, and can provide support information to the surgery room 5 side for performing surgery following the diagnosis thereof.

The remote support surgeon operates the mouse 35 while observing the display device 33. As shown in FIG. 3, operating the mouse 35 displays a cursory image 101 on the display device 33. At this point, the cursor image 101 is only displayed at the remote location side, and is not displayed at the surgery room 5 side.

Operating and unshown first button on the mouse 35 the displays a large-sized cursory image 102 indicating that a cursor display has been made at the surgery room 5 side separate from the cursor image 101, as shown in FIG. 4. At this time, trigger information is transmitted from the second controller 32 to the first controller 24. The trigger information contains at least location information of the cursor image 102, and may include information of the shape and color of thereof, as well.

The first controller 24 synthesizes the image output from the CCU 21 and the cursor image created based on the trigger information from the second controller 32, according to the aforementioned location information. The synthesized image is displayed on the first monitor 22 as shown in FIG. 5, so that at the surgery room 5 side, the endoscope images and the cursor image 102a moving synchronously with the cursor image 102 on the display device 33 can be simultaneously observed on a single monitor, so the problem wherein the working space in the surgery room is reduced by having multiple observation monitors in the surgery room 5 is done away with. That is, the display indicating that the cursor image is displayed on the first monitor 22, is displayed on the display device 33, so the remote support surgeon in the remote surgery room 6 can readily know that instructions are being made to the surgeon in the surgery room 5.

That is, the second controller 32 obtains trigger information for confirming location information from the input means, and transmits the cursor location information at the point that the trigger information was obtained to the first control 24, and the first controller 24 superimposes the cursor image on the endoscope camera image based on the cursor location information received from the second controller 32. Accordingly, the cursor for making marks on the endoscope image in the surgery room 5 can be prevented from moving undesirably and blocking the vision of the surgeon.

Also, the surgeon can perform surgery while observing just one monitor, so there is no need to watch over multiple monitors, as with conventional arrangements. Accordingly, the surgeon can concentrate on the surgery.

According to the present embodiment, the surgeon in the surgery room 5 observes a single monitor and performs surgery, and accordingly can perform surgery while receiving surgery support from a remote location in a natural manner that is no different to normal surgery.

As shown in FIG. 6, in the event that the cursor image 102 moves by operating the mouse 35 while the cursor image 102 is displayed, cursor location information is transmitted to the first controller 24 according to changes in the location of the cursor image 102. In the event that there is change in the received cursor location information, the first controller 24 updates the cursory image 102a of the synthesized image to be output to the first monitor 22 as called for, as shown in FIG. 7.

In the event that the remote support surgeon operates an unshown second button on the mouse 35, the second controller 32 transmits second trigger information to the first controller 224. The second trigger information contains control signals for deleting the cursor display.

That is, the second controller 32 obtains first trigger information for confirming the location information from the input means, and transmits the first trigger information to the first controller 24. The first controller 24 superimposes the cursor image on the image of the endoscope camera and based on the location information at the time of receiving the first trigger information from the second controller 32, and the first controller 24 changes the display location of the cursor image according to location information each time various location information until receiving the second trigger information for deleting the cursor image, from the input means, thereby enabling the cursor image to be displayed at an appropriate location only when needed.

Upon the second trigger information being input to the second controller 32, the second controller 32 transmits the second trigger information to the first controller 24, and also changes the cursor image 102 displayed on the display device 33 to the cursor image 101, as shown in FIG. 8.

Upon receiving the second trigger information, the first controller 24 stops synthesizing the cursor image 102a, and outputs only the endoscope image to the first monitor 22.

Now, with the present embodiment, the difference between the cursor image 101 and the cursor image 102 has been represented by changing the size thereof, but the present invention is by no means restricted to this arrangement, and the difference may be represented by difference in color or shape, or by the display blinking or the like. Also, the cursor image 101 may be erased while displaying the cursor image 102.

Also, the optical endoscope 9 is not restricted to an arrangement wherein an optical image is transferred with the relay lens system, and may use an image guide wherein optical images are sent through a fiber bundle.

Also, though not shown in the figures, the surgeon in the surgery room 5 and the remote support surgeon at the remote control room 6 may exchange audio signals.

Figure 9:
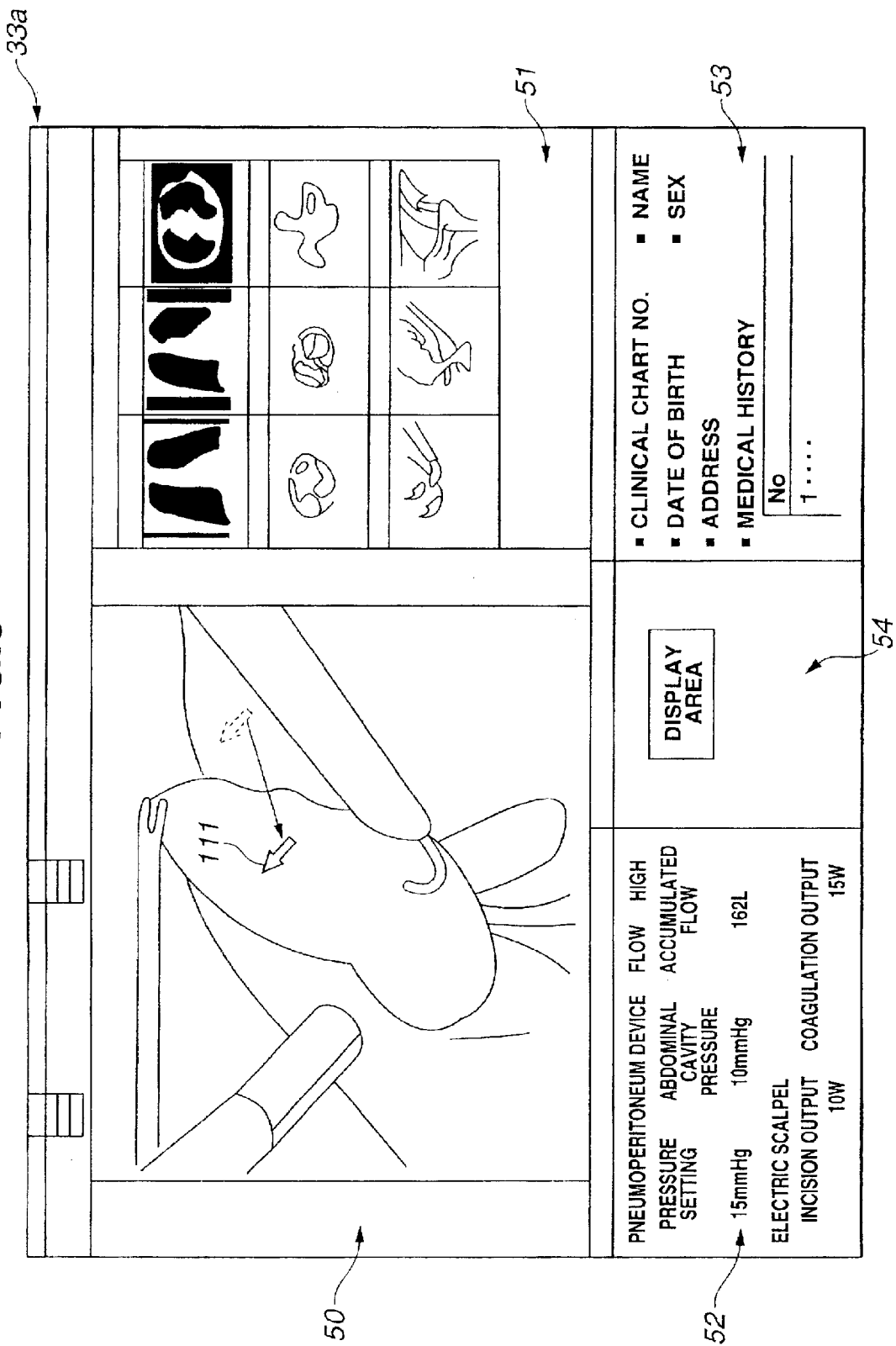
FIG. 9 is a diagram illustrating a first screen display example for describing a cursor displayed on the display screen of a display device according to a second embodiment of the present invention.
Figure 10:
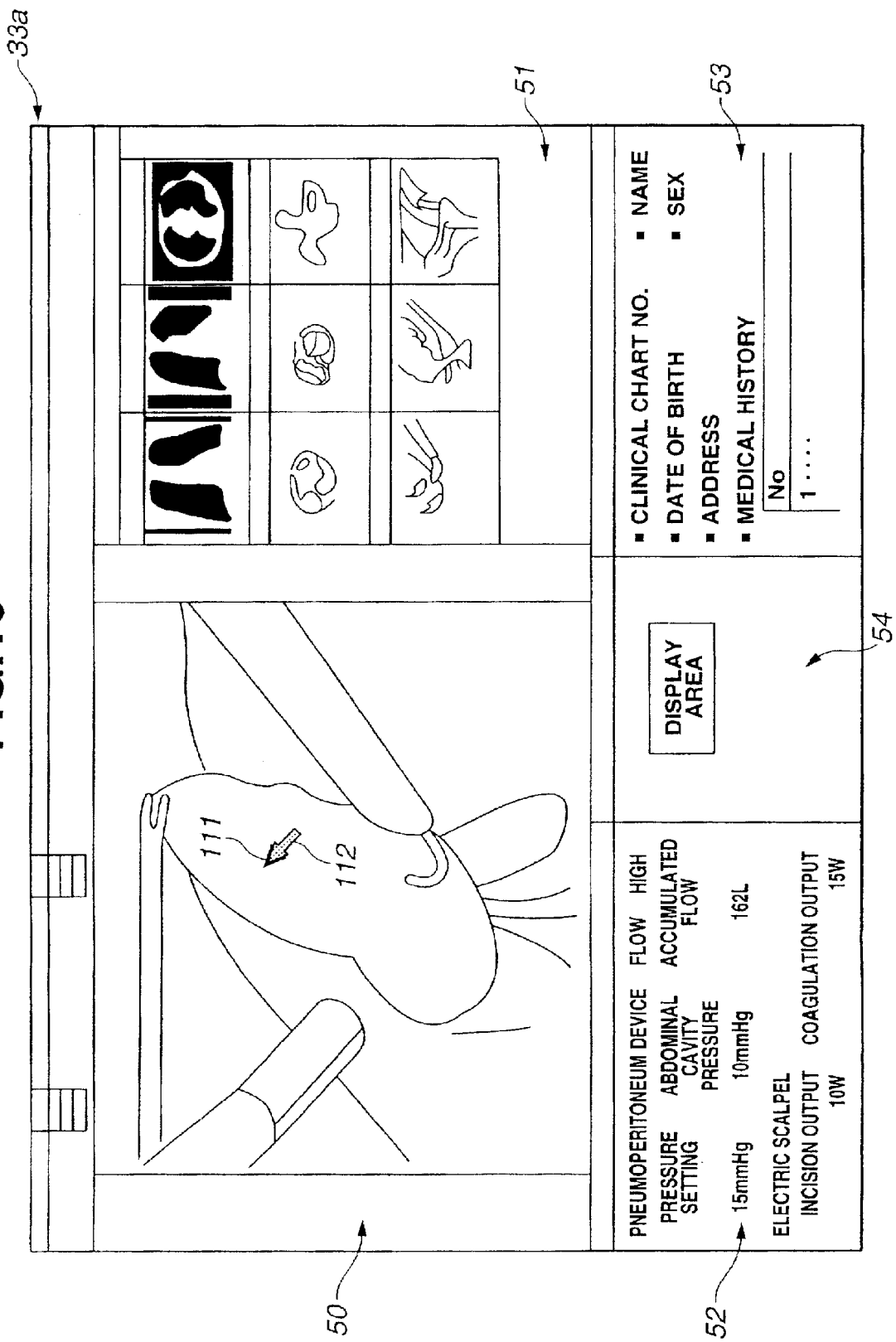
FIG. 10 is a diagram illustrating a second screen display example for describing a cursor displayed on the display screen of the display device shown in FIG. 9.
Figure 11:
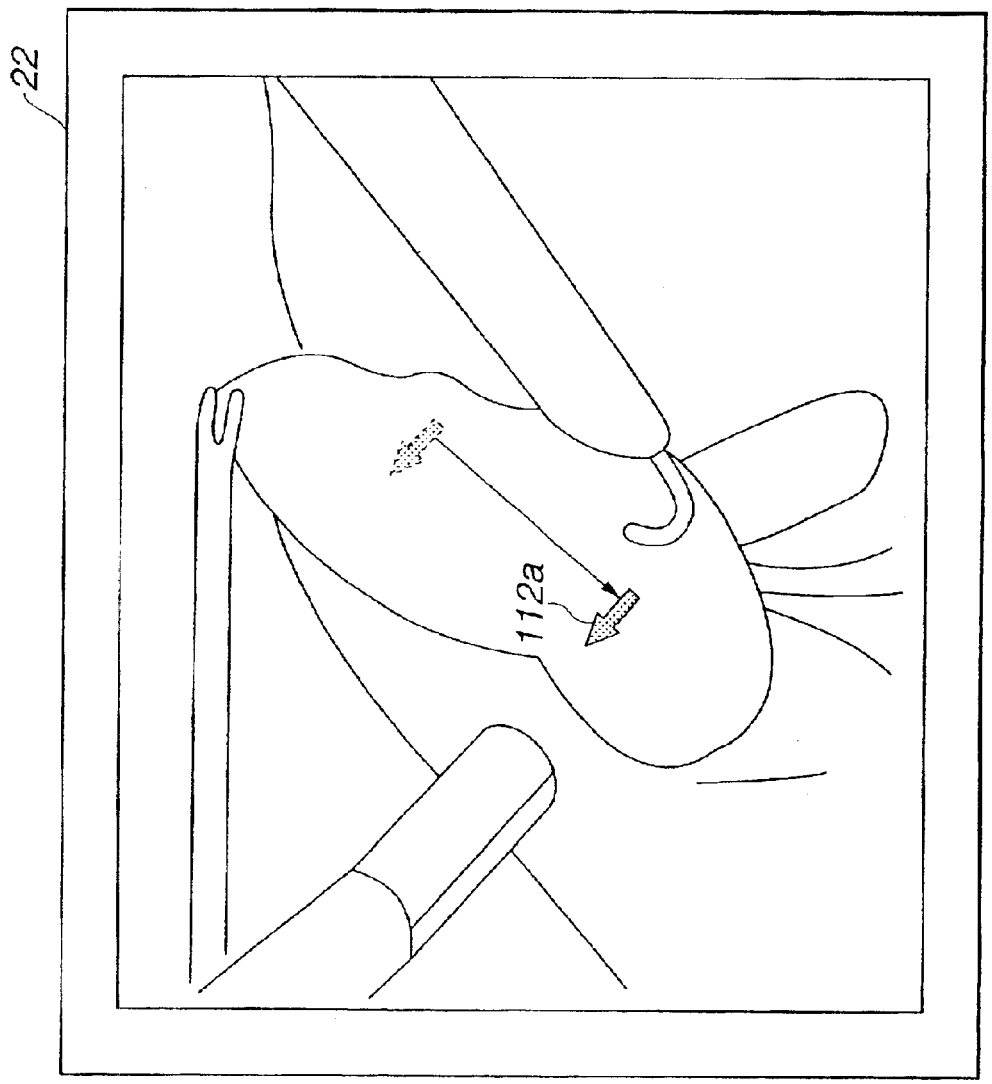
FIG. 11 is a diagram illustrating a first screen display example for describing a cursor displayed on the display screen of the first monitor according to the cursor displayed on the display screen of the display device shown in FIG. 10.
Figure 12:
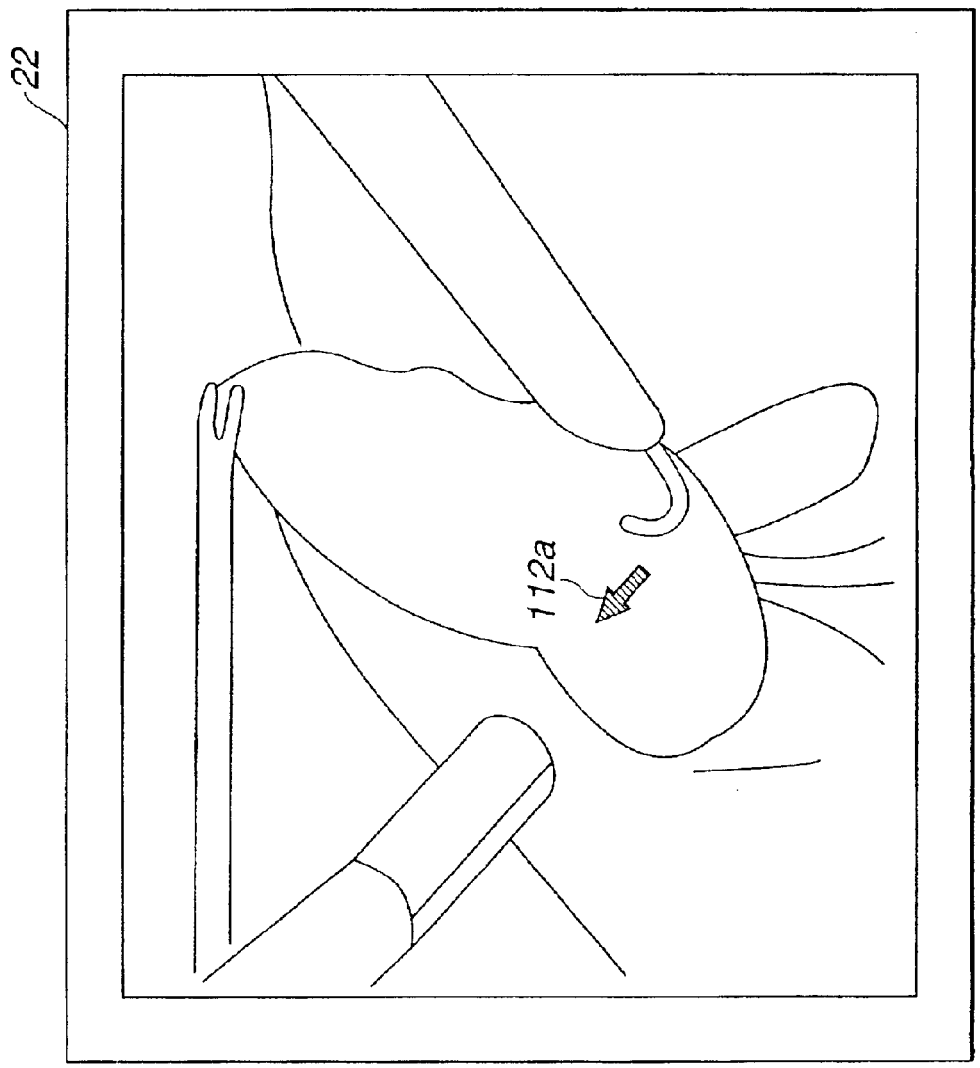
FIG. 12 is a diagram illustrating a second screen display example for describing a cursor displayed on the display screen of the first monitor according to the cursor displayed on the display screen of the display device shown in FIG. 10.

FIGS. 9 through 12 relate to a second embodiment of the present invention, wherein FIG. 9 is a diagram illustrating a first screen display example for describing a cursor displayed on the display screen of a display device according to a second embodiment of the present invention, FIG. 10 is a diagram illustrating a second screen display example for describing a cursor displayed on the display screen of the display device shown in FIG. 9, FIG. 11 is a diagram illustrating a first screen display example for describing a cursor displayed on the display screen of the first monitor according to the cursor displayed on the display screen of the display device shown in FIG. 10, and FIG. 12 is a diagram illustrating a second screen display example for describing a cursor displayed on the display screen of the first monitor according to the cursor displayed on the display screen of the display device shown in FIG. 10.

The second embodiment is almost the same as the first embodiment, so description will be made regarding only the different points, and the components that are the same will be denoted with the same reference numerals, and description thereof will be omitted.

In FIG. 9, a cursor 111 is displayed. This is equivalent to the cursor 101 in the first embodiment, and a cursor is not displayed at the surgery room 5 side. Here, upon the surgeon operating an unshown first button on the mouse 35, a cursor 112 is displayed on the second monitor 33, as shown in FIG. 10. The cursor 112 is displayed with the color different from that of the cursor 111, so that the remote surgeon can readily judge whether or not the cursor is displayed at the surgery room 5 side.

At this time, as with the first embodiment, and as shown in FIG. 11, the endoscope image and a cursor image 112a which moves synchronously with the cursor image 112 on the display device 33 are simultaneously displayed on the first monitor 22, and in the event that there is change in the received cursor location information, the cursor image 102a of the synthesized image to be output to the first monitor 22 is changed at the first controller, as called upon.

Upon the remote support surgeon operating an unshown second button on the mouse 35, the second controller 32 transmits second trigger information to the first controller 24. The second trigger information contains control signals for deleting the cursor display.

Upon the second trigger information being input to the second controller 32, the second controller 32 transmits the second trigger information to the first controller 24, as with a first embodiment, and changes the cursor image 112 to be displayed on the second monitor 33 to the cursor image 111.

As with the first embodiment, the first controller 24, upon receiving the second trigger information, quits synthesizing of the cursor image 112a, and only outputs the endoscope image to the first monitor 22.

Further, upon the remote surgeon operating and unshown third button on the mouse 35, third trigger information containing a new cursor color information is transmitted from the second controller 32 to the first controller 24. That is, by operating the third button on the mouse 35, selection signals for changing the characteristics of the cursor image is transmitted to the second controller 32. As shown in FIG. 12, the first controller 24 changes the color of the cursor image 112a displayed on the first monitor 22 according to the color information of the cursor contained in the third trigger information.

Further, upon the remote surgeon operating the unshown third button on the mouse 35, the first controller 24 further changes the color of the cursor image 112a.

Now, with the present embodiment, the color of the cursor image 112a has been changed by operating the unshown third button of a mouse 35, but it is needless to say that the present invention is not restricted to this arrangement, and the shape or blinking state of the cursor image 112a may be changed.

According to the present embodiment, the remote surgeon can freely change the characteristics of the cursor image 112a displayed on the first monitor 22 and the second monitor 33, so in that event of displaying the cursor image 112a over the endoscope image, the characteristics of the cursor image 112a can be easily changed to facilitate the viewing even in cases wherein the color or shape of the endoscope image and the cursor image 112a are close and difficult to distinguish.

Also, besides endoscope images for diagnosing the state of the patient by remote surgeon, in the event that X-ray images or the like are necessary, that image information can also be transferred to the HDD 41 within the controller 32 at the remote control room 6 side from the controller 24 at the surgery room 5 side.

Note that in the above-described embodiments, arrangements may be made wherein an the remote support surgeon side can also make input for controlling the operations of the surgical equipment, such as setting that output values of the electric scalpel and so forth. That is, with a situation wherein the remote support surgeon can set the values in an easier and more accurate manner, the remote support surgeon side may operate the keyboard 34 or touch panel or the like to transmit control signals to the controller 24 at the surgery room 5 side via the controller 32, thereby controlling the operations of the surgical equipment with the control signals thereof.

Also, in the above-described embodiments, this description has been made regarding an arrangement wherein endoscope images output from the CCU 21 are displayed on the first monitor 22, but arrangement may be made wherein the control contents of the treatment equipment and patient information also input from the controller 24, and these are superimposed and displayed on the endoscope image.

Also, though the above described embodiments use a magnetic card reader 26 as input means for patient information, the present invention is not restricted to this, and may use other information recording media such as IC cards, optical cards, and so forth.

Also, ultrasonic surgical equipment or other such equipment may be suitably used besides the electrical scalpel or pneumoperitoneum device.

Also, the second controller in the remote control room may be arranged so as to send location information to the second signal transmitting device in the event that there has been no change in the location information input from the input means over a predetermined period of time. According to this arrangement, situations wherein the cursor for marking the endoscope images in the surgery room undesirably moves and blocks the surgeon's vision, can be prevented.

Further, the first controller may superimpose the cursor image on the endoscope image in the event that there is no change in the location information received via the first signal transmitting device over a predetermined amount of time. According to this arrangement, situations wherein the cursor for marking the endoscope images in the surgery room undesirably moves and blocks the surgeon's vision, can be prevented.

According to the remote surgery support system relating to the above-described two embodiments, remote surgery support can be facilitated with a good field of view, without deteriorating the surgery environment.

Also, embodiments wherein the above embodiments and the like are partially combined, are also encompassed in the scope of the invention.

As described above, the present invention is advantageous in that endoscope observation images and instruction information from a remote location can be integrated and displayed on a single monitor without inviting deterioration in the working environment of the surgery room, when performing remote surgery support to instruct surgery from a remote location side via a communication line.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgery support system, for performing communication of information regarding surgery, and supporting surgery, said system comprising:

an imaging device for taking images of a treatment region of a patient, and outputting picture signals;

a first display device for displaying images of said treatment region, based on picture signals output from said imaging device;

a first transmitting circuit for transmitting picture signals output from said imaging device to a communication line;

a first receiving circuit for receiving said picture signals from said first transmitting circuit via said communication line;

a second display device for displaying images of said treatment region, based on picture signals received with said first receiving circuit;

a first pointer superimposing circuit for superimposing a first pointer for instructing location on said second display device display said treatment region;

an operating unit for moving said first pointer displayed on said second display device by said first pointer superimposing circuit;

a second transmitting circuit for transmitting location information of said first pointer to said communication line;

a second receiving circuit for receiving location information of said first pointer from said second transmitting circuit via said communication line; and a second pointer superimposing circuit for superimposing a second pointer on said first display device, based on location information received with said second receiving means.

2. A surgery support system according to claim 1, further comprising a transmission control circuit for controlling said second transmitting circuit, based on change in location information of said first pointer which is moved by said operating unit.

3. A surgery support system according to claim 1, further comprising a display control circuit for controlling said second pointer superimposing circuit, based on change in location information received with said second receiving circuit.

4. A surgery support system according to claim 1, wherein the imaging device is provided in an endoscope for observing within a body cavity.

5. A surgery support system according to claim 4, wherein, in the event that there is no change in the location information of said first pointer which is changed by said operating unit for a predetermined amount of time, said first pointer superimposing circuit outputs the location information of said first pointer to said second receiving circuit.

6. A surgery support system according to claim 4, wherein, in the event that there is no change in the location information of said first pointer which is received by said first receiving circuit over a predetermined amount of time, said second superimposing circuit superimposes said second pointer on said images.

7. A surgery support system according to claim 4, wherein said first pointer superimposing circuit inputs trigger information for confirming location information from said operating unit, and outputs the location information of said first pointer at the point that said trigger information is input, to said second receiving circuit.

8. A surgery support system according to claim 4, wherein said first pointer superimposing circuit inputs trigger information for confirming location information from said operating unit, and outputs the location information of said first pointer at the point that said trigger information is input, to said second receiving circuit.

9. A surgery support system according to claim 4, wherein said first controller inputs trigger information for confirming location information from said operating unit, and outputs said trigger information to said second receiving circuit and transmits to said communication line.

10. A surgery support system according to claim 4, wherein said first pointer superimposing circuit inputs trigger information for confirming location information from said operating unit and outputs said trigger information to said second receiving circuit and transmits to said communication line, and wherein said first pointer superimposing circuit inputs said trigger information received from said first receiving circuit by said communication line, and superimposes an image of said second pointer in the images from said endoscope, based on the location information of said first pointer at the point that said trigger information is input.

11. A surgery support system according to claim 10, wherein, during a period from inputting a first trigger information for confirming location information from said operating unit up to inputting second trigger information, said first pointer superimposing circuit outputs said first trigger information to said second receiving circuit.

12. A surgery support system according to claim 10, wherein, in the event that said location information changes during the period from the point of inputting said first trigger information to inputting of said second trigger information, said first pointer superimposing circuit outputs location information as occasion arises.

13. A surgery support system according to claim 10, wherein said operating unit outputs selection signals for changing the characteristics of said pointer image, to said first pointer superimposing circuit.

14. A surgery support system according to claim 13, wherein said operating unit outputs selection signals for changing the characteristics of said pointer image, to said first pointer superimposing circuit.

* * * * *